United States Patent [19]
Krug et al.

[11] Patent Number: 5,827,681
[45] Date of Patent: Oct. 27, 1998

[54] RAPID DETECTION AND DRUG SENSITIVITY OF MALARIA

[75] Inventors: Edward C. Krug, Aurora; Randolph L. Berens, Littleton, both of Colo.

[73] Assignee: University Technology Corporation, Boulder, Colo.

[21] Appl. No.: 771,450

[22] Filed: Dec. 20, 1996

[51] Int. Cl.$^6$ .............. C12Q 1/04; C12Q 1/00; C12N 1/04; G01N 33/53
[52] U.S. Cl. .............. 435/34; 435/4; 435/975; 435/970; 435/260; 435/258.2; 435/258.1; 422/50; 422/55; 422/61
[58] Field of Search .............. 435/34, 4, 975, 435/970, 260, 258.2, 258.1; 422/50, 55, 61

[56] References Cited

PUBLICATIONS

F. Markwardt, "Inventory of Coagulation Inhibitors from Animals Feeding on Blood" 1994 Stuttgart, Thrombosis and Haemostasis 72(3)477–80.

B. Kotecka, K.H. Rieckmann, "An inexpensive and simple method for screening antimalarial drugs" 1992 Stuttgart, Trop.Med.Parasitol.43(1992)9–12.

G. Jamjoon, "Formation and Role of Malaria Pigment" 1988, Review of Infectious Diseases vol. 10, No. 5, pp. 1029–1034 University of Chicago.

G. Jamjoon, "Patterns of Pigment Accumulation in *Plasmodium falciparum* trophozites in Peripheral Blood Samples" 1988 Am.J.Trop.Med.Hyg. 39(1)pp. 21–25 American Society of TropicalMedicine and Hygiene.

C.Lawrence and J. Olson, "Birefringent Hemozoin Identifies Malaria" 1985 Brief Scientific Reports vol. 86, No. 3, pp. 360–363.

G. Jamjoon, "Dark Field Microscopy for Detection of Malaria in Unstained Blood Films" 1983 J. of Clin. Microbiol. vol 17, No. 5, pp. 717–721.

K. Rieckmann, "Visual In–vitro Test for Determining the Drug Sensitivity of *Plasmodium falciparum*" The Lancet, Jun. 12, 1982, pp. 1333–1335.

K. Rieckmann et al., "Drug Sensitivity of *Plasmodium falciparum*" The Lancet, Jan. 7, 1978, pp. 22–23.

*Primary Examiner*—Louise N. Leary
*Attorney, Agent, or Firm*—Biotechnology Patent Services; Ruth Eure

[57] ABSTRACT

A test kit for the rapid detection and drug sensitivity of malaria is presented. The test kit of the present invention comprises a unique microscope/slide incubation chamber which permits rapid detection of malaria in wet blood samples using a regular transmitted light microscope to detect opaque hemozoin particles.

12 Claims, 2 Drawing Sheets

RAPID DETECTION AND DRUG SENSITIVITY OF MALARIA

FIELD OF THE INVENTION

This invention relates to a rapid detection method for plasmodium species (malaria) and determination of drug sensitivity.

BACKGROUND OF THE INVENTION

Malaria is a worldwide health problem in which there are 250 million new cases and 2.1 million deaths each year. There are 4 strains of malaria of clinical significance for humans. Namely, *Plasmodium vivax, P. ovale, P. malariae*, and *P. falciparum*. It is *P. falciparum* which exhibits high mortality and is the primary focus of this invention. *P. falciparum* has a life cycle of 72 hours. The other varieties have a life cycle of about 48 hours. It is critical to detect malaria and analyze its drug sensitivity in a timely manner.

Routine laboratory diagnosis of malaria still relies largely on the microscopic examination of blood films stained with the conventional stains such as Giemsa, Wright stain, Leishman stain, etc. These techniques require examination of the slide under oil. Conventional thin and thick blood films have certain advantages and disadvantages. Thin films only allow the scanning of a relatively small volume of blood and are therefore less sensitive than thick films. They have the advantage, however, of clearly revealing the detailed morphology of the malarial parasites, which is needed for accurate identification of the species.

The current tools for detecting and/or quantifying malaria rely on stained blood smears as the mainstay with the recent addition of an array of specialized techniques of DNA PCR, antigen capture test, enzyme linked immunosorbant assay (ELISA), monoclonal antibody immunofluorescence ParaSight-F test, indirect fluorescence antibody test, quantitative buffy coat analysis, radioactive substrate incorporation, or detection of the particulate opaque, insoluble heme detoxification pigment, hemozoin, by use of birefringence with polarized light microscopy with an addition of magnetic enrichment, or by dark field microscopy, or by the visible hemozoin's residue following alkali digestion of the infected erythrocytes.

The malarial pigment, hemozoin, is a crystalline product of the digestion of hemoglobin by the parasites. It first appears in the late ring forms and is abundant in the intermediate and late asexual forms and gametocytes of all human malarias. It is the presence of hemozoin which is relied upon as the detection mechanism of the present invention.

One handicap in working with the intraerythrocytic stage of malaria is that there is no technique for non-destructively viewing the parasite. This adds time consuming steps to *P. falciparum* culture when compared to culturing of the other parasitic protozoa whose growth in culture can be assessed with simple phase contrast microscopy. This same handicap also encumbers the assessment of malaria drug sensitivity or screening of potential antimalarials, so much so that assessment of *P. falciparum* drug sensitivity is neither technically or economically feasible in most clinical settings.

The disturbing rate at which malaria parasites are becoming resistant to antimalarial drugs emphasizes the need for a standardized test kit which can be readily used by medical and laboratory personnel to determine the parasite's susceptibility to various drugs. This invention utilizes a method based on hemozoin detection which allows continuous *P. falciparum* culture without any other assessment of parasitemia or growth. This basic technique is also applied to assessing inhibition of *P. falciparum* growth in screening potential antimalarials and sensitivity of *P. falciparum* to selected antimalarial compounds.

The basic method presented herein is further applied in a device which permits sterile 4day malaria culture and detection in field conditions with no exotic facilities beyond a simple light microscope and 37° C. candle jar.

SUMMARY OF THE INVENTION

This invention teaches a new test kit that will provide a means of detecting malaria immediately or up to 24 hours and assess drug sensitivity in about 3 to 4 days with no more than a microscope. The test kit of the present invention has a substantial shelf life and is economical to produce.

It is an object of the present invention to provide an economical method and apparatus to screen a person's blood for the presence of malaria.

It is an object of the present invention to provide an economical method and apparatus to screen a person's blood for the presence of malaria and determine sensitivity to known antimalarial compounds.

It is a further object of the present invention to provide an economical method and apparatus for said screenings which uses any standard light microscope.

It is an object of the present invention to provide a method of maintaining, establishing and harvesting a malaria culture.

It is a further object of the present invention to provide a means to conveniently transport a malaria culture.

The present invention teaches a method which uses a unique microscope slide/incubation chamber which permits rapid detection of malaria in wet blood samples using regular transmitted light illumination of a wet whole blood sample preparation by detection of the opaque hemozoin particles which are the byproduct of hemoglobin metabolism by the parasite. The presence of this particle is indicative of the presence of Plasmodium species indicating malaria infection.

The invention is comprised of multiple chambers, the first is a blood collection chamber, the second mixing chamber contains growth medium and a diluent, and the remaining chambers contain additional culture media as well as antimalarial compounds selected to be specific to the geographic region of interest. The antimalarial compounds are present in concentrations appropriate to assess the sensitivity of the patient's malaria to the drug in that chamber. The detection method relies upon the relative amount of hemozoin particles relative to the drug free control chamber. The change in number and cluster distribution of new hemozoin particles is an indication of malaria growth and is used to determine drug resistance.

The chambers consist of two plastic films fused together in a pattern so the resulting bilayer contains several cavities to contain selected ingredients and tubes to interconnect the chambers. The device is designed to detect hemozoin particles with no facilities other than an alcohol swab to sterilize a finger, a finger prick lance to draw some blood, a candle size flame provided by any appropriate means such as a match, a candle, a Bunsen burner, or butane lighter, a pocket knife and a malaria culture candle jar. The blood sample contains the serum components necessary for malaria culture.

The method of the present invention uses a unique microscope slide/incubation chamber which permits rapid detection of malaria in wet blood samples using regular transmitted light illumination of a wet whole blood sample preparation by detection of the opaque hemozoin particles.

The chambers consist of two inexpensive plastic films fused to contain several cavities containing selected ingredients and tubes connecting the chambers. The conformation of the device is designed to optimize visualization of the hemozoin particles with no facilities other than a standard light microscope.

DETAILED DESCRIPTION OF THE PREFERRED EMBODIMENT

The following description is to be construed as illustrative in nature and any variations or modifications which would be obvious to one skilled in the art are considered to fall within the spirit and scope of this invention.

The malaria test kit of the present invention is described below. It comprises two layers, at least one of which is made from breathable film to form a bilayer which is heat fused in a pattern to form a system of blister cavities, several sections of capillary tube, and a vent to contain a plug of air-permeable, liquid-impermeable material. One blister contains dry ingredients and another blister contains wet ingredients, which, when mixed together comprise a complete culture medium. The blood sample, along with this complete culture medium is transferred to the incubation chambers. With this system, a blood sample taken from a sterile finger stick can be tested for the presence of malaria immediately, and, if negative, reexamined within 24 hours to determine the presence of hemozoin, thereby indicating malaria infection. Sensitivity to a variety of antimalarial compounds can be determined after 3 to 4 day's incubation.

Figure 1:
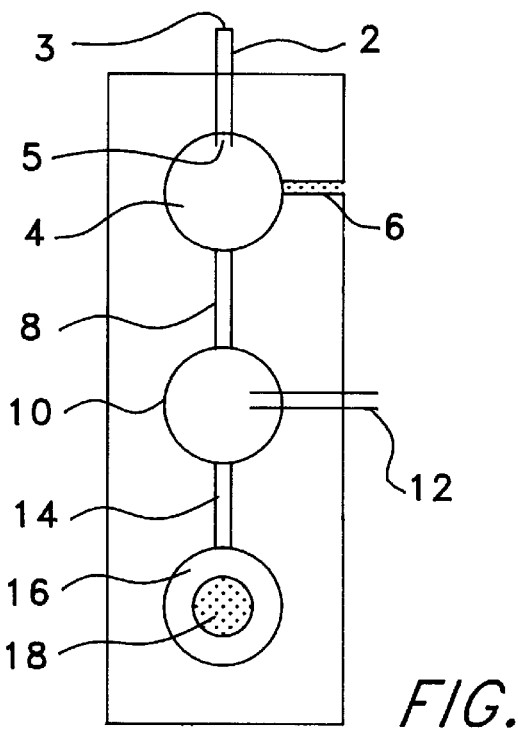
FIG. 1 is a front view of the test kit of the present invention.
Figure 2:
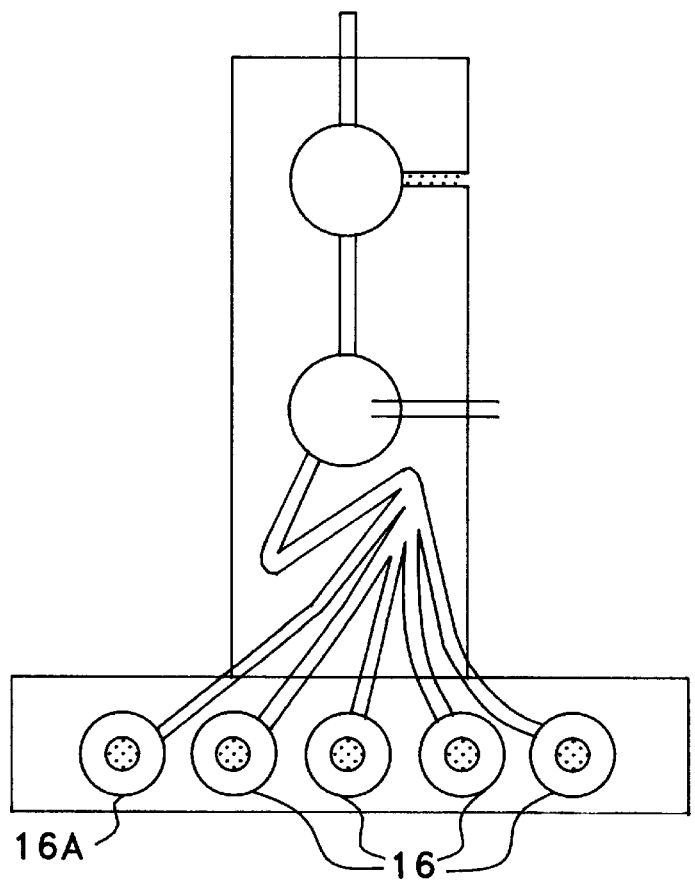
FIG. 2 is a front view of a modified form of the test kit of the present invention.
Figure 3:
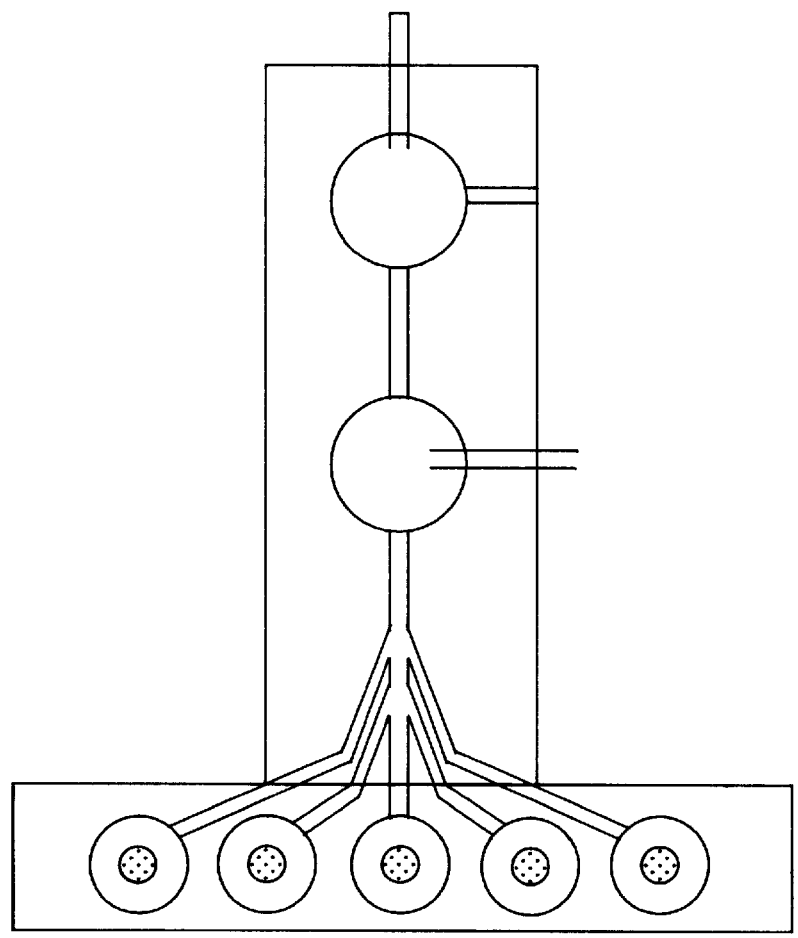
FIG. 3 is a front view of an additional modified form of the test kit of the present invention.
Figure 4:
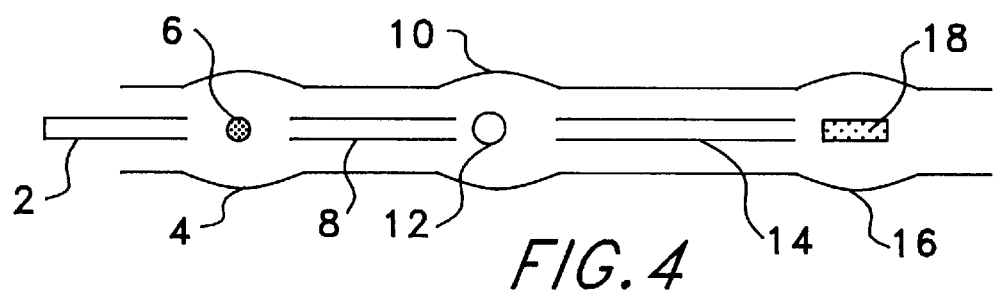
FIG. 4 is a side view of the test kit of the present invention.
Figure 5:
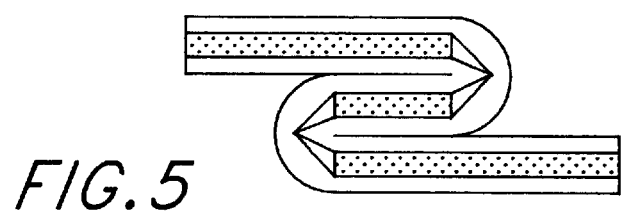
FIG. 5 is a front view of the S-shaped configuration in the connecting capillary tubes.

Turning more specifically to FIGS. 1 and 2, the test kit of the present invention comprises:

A filling capillary tube 2 is used for addition of whole blood, the external end 3 of which is sealed to preserve sterility until cut and heat resealed after the addition of the blood.

The internal end 5 of filling capillary tube 2 opens into filling blister chamber 4. Filling blister chamber 4 serves as the chamber for receiving the blood sample. Filling blister chamber 4 is vented from one side by a capillary vent tube 6 which is blocked with a plug of an expandable matrix material which allows the expulsion of air from chamber 4 during filling and which produces a sterile bacterial seal when wet. Examples of suitable expandable matrix material include diatomaceous earth or bentonite clay. Hydrophobic membranes such as ACRO 37TF from Gelman Sciences, Inc., Ann Arbor, Mich., are also suitable for use as the vent plug.

After sterile filling of filling blister chamber 4 with whole blood, the end of filling capillary tube 2 is heat sealed.

All of the chambers and tubes which come in contact with the blood can contain an anti-coagulant, if desired. The anticoagulant must be stable when dry, highly soluble for ease of transfer of the sample between the chambers, be effective for at least four days and not interfere with the growth and replication of *P. falciparum*. Anticoagulants which may meet this purpose include, but are not limited to: heparin, citrate, EDTA, ixodin, ixin, argasin, prolixin, triatomin, maculatin, reduviin, rhodniin, rhokinase, apyrase, pallidipin, tabanin, hirudin, destabilase, bufrudin, antistasin, hementin, decorsin, ancylostomatin, calin, ghilantin. See Markwardt, *Thrombosis and Haemostasis*, 72(3):477–480.

A connecting capillary tube 8 connects filling blister chamber 4 to mixing blister chamber 10. Mixing blister chamber 10 contains a diluent containing a stable base medium. The combination of the liquid medium from mixing chamber 10 with the dry ingredients from incubation chambers 16 results in a complete culture medium adequate for four days'of *P. falciparum* growth. The plasma contained in the patient's whole blood sample provides the serum ingredients normally found in malaria cultures.

Filling of filling blister chamber 4 is done by first sterilizing the end of filling capillary tube 2 with application of a sterilizing agent compatible with malaria growth such as alcohol. The end of filling capillary tube 2 is cut by a sterile knife, touched to a pool of blood to the incubation chambers 16. This is accomplished by pressing on the contents of mixing blister chamber 10 through the film so as to direct the flow of said contents into incubation chambers 16. One of incubation chambers 16 serves as a control chamber and is designated 16A. Control chamber 16A contains only the dry ingredients to complete the growth medium and contains no antimalarial compound. Control chamber 16A is the control chamber which is used for detection of malaria as well as the control for comparison to the other incubation chambers 16 to determine the sensitivity of the malaria to the antimalarial compounds present in the remaining incubation chambers 16. Except for the control chamber 16A, each of the other incubation chambers 16 contain an antimalarial compound which are candidates for therapeutic administration. Compounds suitable for this purpose include, but are not limited to: doxycycline, mefloquine, chloroquine, quinine, fansidar, primaquine, artemisin, halofantrine, atovaquone, proquanil, azithromycin, atabrine, aralen, plaquenil, pyrimethamine, sulfadoxine, quinachrine, lariam, and derivatives thereof. These compounds can be in the form of a powder, a tablet or a wafer of fibrous material which is impregnated with the compound in lyophilized or other form. In addition to the candidate antimalarial compound, incubation chambers 16 also contain the dry ingredients necessary to complete the culture medium for 4 days'*P. falciparum* growth. Incubation chambers 16 are used for incubation of the culture as well as a viewing vessel for malaria growth. To enhance viewing, incubation chambers 16 are configured to allow a gradation of thickness of sample. This chamber is comprised of at least one layer of breathable film, such as polyester foil available from Sarstedt, Inc., Newton, N.C. Incubation chambers 16 can be manufactured so as to be detachable from the remainder of the kit for ease of microscopic viewing.

Filling blister chamber 4 is manufactured to be flat and empty but with the addition of blood it will fill to a specific size and volume. This volume of blood when mixed with other liquid in the kit will give appropriate dilutions of reagents, cells and plasma for effective malaria growth and viewing.

Once the contents have been mixed as described above, incubation chambers 16 are sealed off from mixing chamber 10 and the system is incubated for 4 days in a candle jar at 37° C. in a manner known by those familiar to the art of malaria culture.

The laminated edges of the blister chamber system may have an adhesive applied to its surface which has a peel-away cover such that the entire unit can be affixed to a microscope slide. This allows for stable handling and good presentation during microscopic examination. The growth of the malaria is visually assessed after an initial incubation period. The change in number and cluster distribution of hemozoin particles relative to the drug free-control incubation chamber 16A is an indication of malaria growth and drug resistance.

At the time of fabrication of the device, a section of the capillary tube 14 between the blister chambers contains an S-shaped fold which produces a kink in the tubing. This kink is stabilized by a layer of non-permanent adhesive so that the kink can be unfolded and the S-shape in the tubing can be unfolded for mixing and refolded in its S-shape to seal off the contents of mixing chamber 10 from the contents of incubation chambers 16.

This tubing may be made of a material more rigid than the layer of film such that the S-shape is sufficient to stop the flow of contents from one chamber to the other.

At the time of manufacture, mixing blister chamber 10 is formed to be accessible by an additional access tube 12. Additional access tube 12 is made of higher melt material, through which the liquid contents can be added, and then heat sealed. Mixing blister chamber 10 is filled with a fixed amount of incubation medium containing the stable ingredients.

Incubation is carried out at 37° C. After an appropriate incubation period, the contents of incubation chambers 16 are examined microscopically for the amount of hemozoin present to determine if malarial infection is present, and if so, if it is sensitive to any of the anti-malarial compounds offered in incubation chambers 16. An appropriate magnification for this purpose is 200×.

In addition to the above, the malaria culture can be harvested from incubation chambers 16 for further characterization or culture. This method of establishing, maintaining and harvesting a malaria culture from a blood sample using the test kit of the present invention comprises collecting a blood sample from a patient; putting the blood sample into the test kit; mixing the blood sample with culture media in the test kit; incubating the blood sample mixed with the culture media to make a culture; maintaining the culture for about four days; and harvesting the culture from the test kit.

Although the foregoing description has set forth specific embodiments, the present inventors do not wish to be limited thereto and any modifications and variations which would be obvious to the skilled artisan are intended to be included herein.

We claim:

1. A test kit for detecting the presence of a malarial infection in a blood sample and determining sensitivity of the malarial infection to an anti-malarial compound comprising:

a bottom layer and a top layer; said bottom layer and said top layer being fused together so that said fusing forms a pattern which creates a plurality of blister chambers connected to each other by connecting tubes wherein at least one of said layers is comprised of breathable film, and the test kit is dimensioned to be used with a light microscope; and wherein a first blister chamber having an inlet tube and a vent tube is designed to receive a blood sample; and wherein a second blister chamber is connected to said first blister chamber by a non-permanent seal and said second blister chamber contains liquid culture media and diluent and a vent tube;

and a third blister chamber is connected to said second blister chamber by a non-permanent seal and said third blister chamber contains an antimalarial compound.

2. The test kit of claim 1 wherein the antimalarial compound is lyophilized and impregnated onto a fibrous wafer.

3. The test kit of claim 1 wherein the antimalarial compound is a powder.

4. The test kit of claim 1 wherein the antimalarial compound is in the form of a tablet.

5. The test kit of claim 2 wherein the impregnated fibrous wafer dissolves when mixed with liquid culture media.

6. The test kit of claim 2 wherein the impregnated fibrous wafer does not dissolve when mixed with liquid culture media.

7. A method for detecting the sensitivity of a malarial infection to an antimalarial compound using the test kit of claim 1.

8. The test kit of claim 1 wherein said third chamber is divided into a plurality of chambers.

9. The test kit of claim 1 wherein said third chamber is divided into 5 chambers.

10. The test kit of claim 1 wherein said antimalarial compound is selected from the group consisting of: doxycycline, mefloquine, chloroquine, quinine, fansidar, primaquine, artemisin, halofantrine, atovaquone, proquanil, azithromycin, atabrine, aralen, plaquenil, pyrimethamine, sulfadoxine, quinachrine, lariam and derivatives thereof.

11. A method of establishing, maintaining and harvesting a malaria culture from a blood sample comprising:

collecting a blood sample from a patient;

injecting the blood sample into the test kit of claim 1;

mixing the blood sample with culture media in the test kit;

incubating the blood sample mixed with the culture media to make a culture;

maintaining the culture for about four days;

harvesting the culture from the test kit.

12. A method for determining the presence of malarial infection in a patient and determining the sensitivity of the infection to known antimalarial compounds comprising:

collecting a blood sample from a patient;

injecting the blood sample into the test kit of claim 1;

mixing the blood sample with culture media in the test kit;

incubating the blood sample mixed with the culture media to make a culture;

maintaining the culture for about four days;

viewing the culture for the presence of hemozoin particles;

determining the presence of malaria and sensitivity to antimalarial compounds by viewing and comparing the amount of hemozoin particles.

* * * * *